(12) United States Patent
Schabbach et al.

(10) Patent No.: US 11,911,591 B2
(45) Date of Patent: Feb. 27, 2024

(54) DISPOSABLE CARTRIDGE FOR A DRUG DELIVERY DEVICE

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1004 days.

(21) Appl. No.: 15/104,855

(22) PCT Filed: Dec. 18, 2014

(86) PCT No.: PCT/EP2014/078413
§ 371 (c)(1),
(2) Date: Jun. 15, 2016

(87) PCT Pub. No.: WO2015/091761
PCT Pub. Date: Jun. 25, 2015

(65) Prior Publication Data
US 2016/0310662 A1   Oct. 27, 2016

(30) Foreign Application Priority Data
Dec. 20, 2013   (EP) .................................... 13198767

(51) Int. Cl.
*A61M 5/148*       (2006.01)
*A61M 5/142*       (2006.01)
*A61M 5/152*       (2006.01)
*A61M 5/158*       (2006.01)

(52) U.S. Cl.
CPC ...... *A61M 5/1483* (2013.01); *A61M 5/14228* (2013.01); *A61M 5/14232* (2013.01);
(Continued)

(58) Field of Classification Search
CPC .. A61M 5/148; A61M 5/1483; A61M 5/2425; A61M 5/2422; A61M 5/1486;
(Continued)

(56) References Cited

U.S. PATENT DOCUMENTS 2,805,662 A * 9/1957 Lawshe ............... A61M 5/2425
604/204
3,459,337 A * 8/1969 Williamson .......... A61M 5/142
222/183
(Continued)

FOREIGN PATENT DOCUMENTS

| CN | 2379686 | 5/2000 |
|---|---|---|
| CN | 101799094 | 8/2010 |

(Continued)

OTHER PUBLICATIONS

International Search Report and Written Opinion in International Application No. PCT/EP2014/078413, dated Mar. 24, 2015, 11 pages.

(Continued)

*Primary Examiner* — Brandy S Lee
*Assistant Examiner* — Hong-Van N Trinh
(74) *Attorney, Agent, or Firm* — Fish & Richardson P.C.

(57) ABSTRACT

A disposable cartridge for a drug delivery device includes a flexible bag to accommodate a liquid medicament and having an opening adjacent to a sidewall, a socket having a fluid channel in fluid communication with a cartridge fluid coupling, and a housing covering at least a portion of the flexible bag and having a receptacle to receive the socket with the flexible bag. The socket extends into the opening of the flexible bag. The flexible bag's sidewall is fixed between the socket and the receptacle.

19 Claims, 10 Drawing Sheets

(52) U.S. Cl.
CPC ............ *A61M 5/152* (2013.01); *A61M 5/158* (2013.01); *A61M 2205/12* (2013.01)

(58) Field of Classification Search
CPC ................ A61M 5/152; A61M 1/1039; A61M 5/14228; A61M 5/14232; A61M 5/14; A61M 5/142; A61M 5/158; A61M 2205/12; A61M 5/14244; A61M 5/14248; A61M 2005/14268; F04B 43/12; A61J 1/00; A61J 1/10; A61J 1/12; A61J 1/1406; A61J 1/14; A61J 1/1412; A61J 1/1475; A61J 1/16; A61J 1/05; A61J 1/1425; B65D 83/0055
See application file for complete search history.

(56) References Cited

U.S. PATENT DOCUMENTS

| | | | | |
|---|---|---|---|---|
| 3,486,539 | A | * | 12/1969 | Candido ............... A61M 5/162 141/329 |
| 3,785,367 | A | * | 1/1974 | Fortin ................. A61B 5/1535 600/576 |
| 4,273,260 | A | | 6/1981 | Bush |
| 4,769,008 | A | * | 9/1988 | Hessel ................. A61M 5/152 222/211 |
| 5,718,334 | A | * | 2/1998 | Demel ................. A61F 9/0008 206/222 |
| 2006/0069382 | A1 | * | 3/2006 | Pedersen .............. A61K 9/0004 604/890.1 |
| 2009/0214364 | A1 | * | 8/2009 | Wex ..................... A61M 5/152 417/474 |
| 2010/0137808 | A1 | | 6/2010 | Wilmot et al. |
| 2011/0144586 | A1 | | 6/2011 | Michaud et al. |

FOREIGN PATENT DOCUMENTS

| | | | | |
|---|---|---|---|---|
| CN | 202691384 | | 1/2013 | |
| EP | 1384490 | | 1/2004 | |
| EP | 2229927 | | 9/2010 | |
| GB | 214486 | A * | 4/1924 | ............ C10B 25/08 |
| GB | 2214486 | | 9/1989 | |
| JP | S57-197942 | | 12/1982 | |
| JP | H09-308694 | | 12/1997 | |
| JP | 2002-159572 | | 6/2002 | |
| JP | 2003-180826 | | 7/2003 | |
| JP | 2003-180827 | | 7/2003 | |
| JP | 2005-137491 | | 6/2005 | |
| JP | 2007-075368 | | 3/2007 | |
| JP | 2009-523465 | | 6/2009 | |
| JP | 2009-153985 | | 7/2009 | |
| JP | 2009-533145 | | 9/2009 | |
| JP | 2010-180969 | | 8/2010 | |
| JP | 2013-526333 | | 6/2013 | |
| JP | 2013-216902 | | 10/2013 | |
| WO | WO 03/008023 | | 1/2003 | |
| WO | WO2004/009159 | | 1/2004 | |
| WO | WO 2007/056233 | | 5/2007 | |
| WO | WO2007/120641 | | 10/2007 | |
| WO | WO 2011/142831 | | 11/2011 | |

OTHER PUBLICATIONS

International Preliminary Report on Patentability in International Application No. PCT/EP2014/078413, dated Jun. 21, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

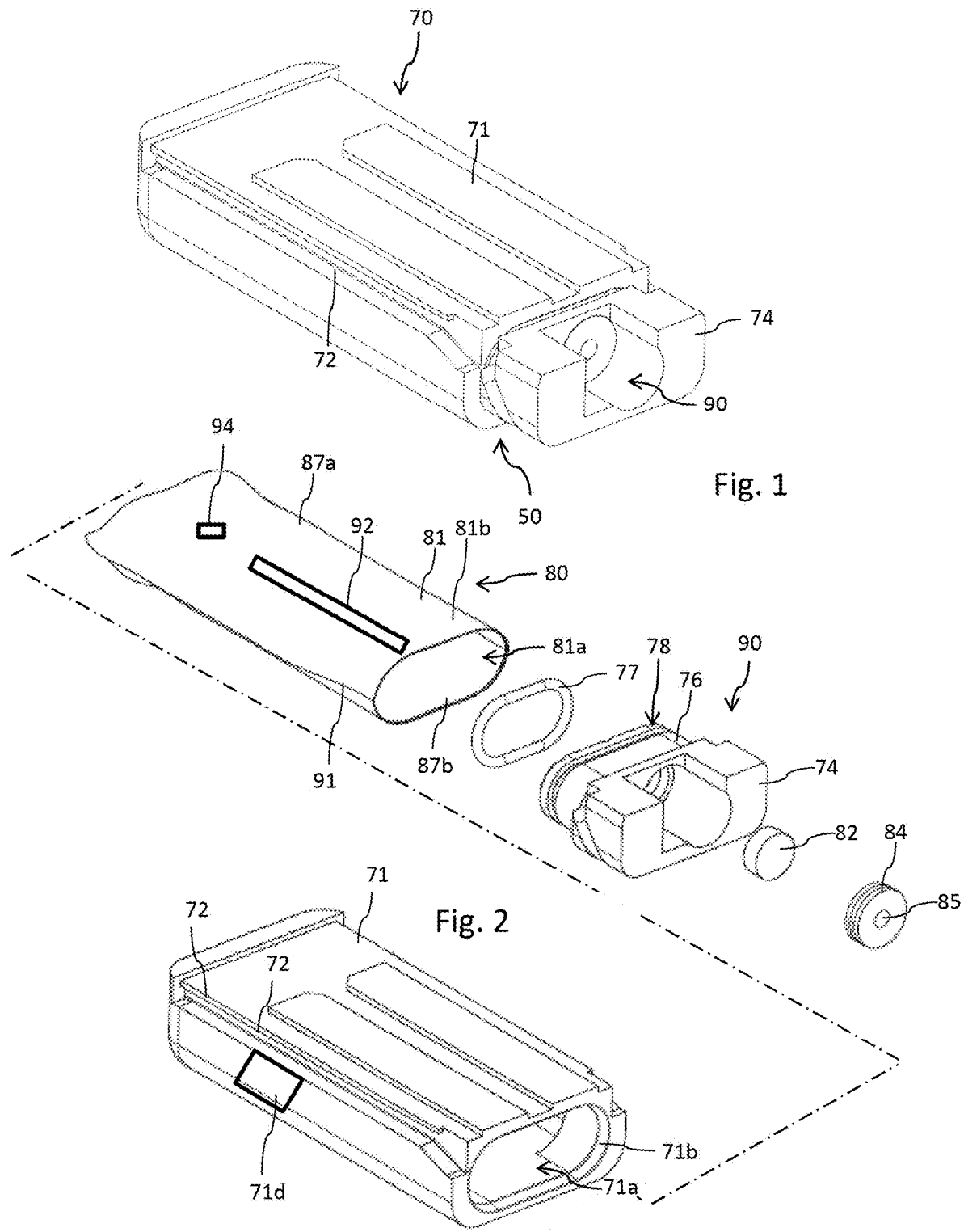

DISPOSABLE CARTRIDGE FOR A DRUG DELIVERY DEVICE

CROSS-REFERENCE TO RELATED APPLICATIONS

This application is a U.S. national stage application under 35 USC § 371 of International Application No. PCT/EP2014/078413, filed on Dec. 18, 2014, which claims priority to European Patent Application No. 13198767.9, filed on Dec. 20, 2013, the entire contents of which are incorporated herein by reference.

TECHNICAL FIELD

The present disclosure relates to the field of cartridges for liquid medicaments and in particular to cartridges containing a reservoir to receive and to extract a liquid medicament. The disclosure further relates to cartridges that are applicable for long-term storage as well as for administering the liquid medicament by means of a drug delivery device. The disclosure also relates to a respective drug delivery device equipped with such a cartridge.

BACKGROUND

Drug delivery devices for administering liquid medicaments are widely known in the art. Parenteral administering of liquid medicaments is typically conducted by means of injection devices, such like syringes, pen-type injectors or by means of infusion pumps, e.g. by way of micropumps.

For treatment of chronic diseases, such like diabetes the medicament has to be regularly administered according to a predefined schedule. Known drug delivery devices may either be adapted for discrete use for injecting of a pre-defined amount of the medicament a given number of times during the day. Alternatively, such drug delivery devices may be adapted for continuous or quasi-continuous delivery of the medicament through a permanent fluid connection between the delivery device and the patient. Continuous or constant administering of the medicament is typically conducted by means of infusion pumps that are relatively expensive.

Such drug delivery devices typically comprise a reservoir to accommodate the liquid medicament and having an outlet in fluid communication with some kind of infusion or injection needle. Moreover, such drug delivery devices also comprise a drive mechanism that is operable to expel or to withdraw a predefined amount of the liquid medicament from the reservoir and through the infusion or injection needle into biological tissue of the patient.

There exist reusable as well as disposable devices, wherein with reusable devices the medicament-containing reservoir is to be replaced when empty. With disposable drug delivery devices a pre-filled reservoir is non-detachably arranged in the device. When the medicament contained therein has been used up the entire device is intended to be discarded.

Traditionally, vitreous or glass cartridges have been widely used in injection or infusion systems to contain or to accommodate the liquid medicament, hence a particular pharmaceutical composition. Glass cartridges or carpules provide a large degree of optical transparency and are substantially inert to the medicament. This means, that substantially no interaction between the medicament and the glass cartridge takes place even under long term storage conditions, i.e. when the medicament is stored and contained in the cartridge for time intervals of severely years.

Additionally, the optical transparency of the glass cartridge allows the patient to visually check the quality and integrity of the medicament. Additionally, glass provides an excellent barrier against ingress of liquid or gaseous media from the environment into the cartridge. Moreover, vitreous or glass bodies of cartridges effectively prevent leakage of the medicament from the cartridge. Therefore, vitreous cartridges or glass cartridges are widely used for long-term storage of liquid medicaments. Such cartridges pre-filled with a liquid medicament can be stored over comparatively long time intervals and may be readily assembled with or into a drug delivery device for direct delivery of the medicament from the cartridge into biological tissue of the patient.

Vitreous cartridges or glass cartridges are prone to mechanical impact and may therefore represent a concern for patients but as well for the pharmaceutical industry. Glass breakage typically represents a hazard for the patient as well as for the industrial production environment. Moreover, handling of broken glass is quite risky and dangerous for the persons concerned with a broken cartridge.

Especially with highly concentrated medicaments and with infusion pumps comparatively small volumes have to be injected or low volume flow rates have to be realized. Existing micro pump or peristaltic pump systems already make use of exchangeable and flexible medicament containers. With flexible reservoirs such like foil bags or film pouches the medicament located and stored therein may be withdrawn by way of suction. With flexible bags featuring a high degree of flexibility pump power and energy consumption of a pumping mechanism can be kept at a rather low level. However, with flexible bags the inevitable and intended folding behavior of such bags may cause problems in that the outlet of such a reservoir may be at least partially covered and hence obstructed by a flexible and inwardly-bended portion of the bag itself.

In addition it is rather elaborate to provide substantially bubbleless filling or charging of such reservoirs with a liquid medicament. Moreover, the fluid transferring coupling and replacement of such flexible reservoirs may be rather sophisticated and requires improvement with regard to general handling and patient safety. In addition, the sealing of such flexible reservoirs may be somewhat complicated in that typical sealing techniques require application of heat or use of an adhesive, which may both deteriorate or degrade the stability and quality of the medicament stored therein. Hence, a long term stability and the guaranteed shelf life of the medicament may suffer.

SUMMARY

In certain aspects of the present invention, a disposable cartridge for a drug delivery device features a flexible bag that may overcome the above mentioned disadvantages.

In a first aspect, a disposable cartridge for a drug delivery device is releasably attachable with the drug delivery device and contains a liquid medicament to be dispensed by the drug delivery device. Typically, the disposable cartridge is configured and adapted to be releasably coupled with an injection device, such like a peristaltic pump. The cartridge comprises a flexible bag to accommodate a liquid medicament. The flexible bag comprises a sidewall and an opening located adjacent to the sidewall. The cartridge further comprises a socket having a fluid channel being in fluid communication with a cartridge fluid coupling. The socket extends into the opening of the flexible bag. Typically, the socket closes and seals the opening of the flexible bag. In other words, the rigid socket provides a mount and a base for the flexible bag allowing for a well-defined assembly of the flexible bag to or in the cartridge and allowing for a well-defined and precise coupling of the cartridge with an injector fluid coupling of a disposable injector or with another fluid transferring component of the drug delivery device. In particular, with a rigid housing of the cartridge, a well-defined, easy and intuitive assembly of the cartridge to a drug delivery device can be provided.

Moreover, the disposable cartridge comprises a housing covering at least a portion of the flexible bag and having a receptacle to receive the socket with the flexible bag attached thereto. With the housing receiving the socket the flexible bag's sidewall is fixed between the socket and the receptacle. By way of the mutual engagement of housing and socket the flexible bag can be securely attached and fixed to the socket as well as to the housing. Typically, the flexible bag's sidewall adjacent to the opening is squeezed or clamped between the housing and the socket of the cartridge. In this way the flexible bag can be sealed. In addition, the flexible bag can be mounted and fixed to the arrangement of socket and housing.

By arranging and fixing the flexible bag's sidewall between the socket and the circumferential receptacle a purely mechanically implemented seal can be provided. It is neither necessary to make use of adhesives or some kind of welding procedure nor to apply heat to the flexible bag for effectively sealing the same. In this way, application of thermal energy or use of adhesives or sealing agents can be avoided. Potential detrimental effects that may arise from thermal energy deposition or from the use of adhesives or sealing agents can be eliminated. In effect, the quality of the medicament located in the disposable cartridge and hence patient safety can be enhanced and improved. Moreover, by implementing of a purely mechanical seal and a respective mechanical engagement of flexible bag, socket and housing the process of manufacturing and assembly of the disposable cartridge may be simplified and may become more cost efficient.

According to an embodiment the flexible bag is sealingly fitted between an outside facing portion of the socket and an inside facing portion of the housing. Typically, the socket may be of cylindrical shape and may feature a front face extending into the flexible bag and having a circumferential outside facing surface or outside facing portion to at least partially engage with a correspondingly-shaped inside facing portion of the housing. Consequently, also the housing may be of substantially cylindrical shape and typically features an inside facing sidewall portion that matches and mates with the outside facing portion of the socket. Outside facing portion of the socket and correspondingly-shaped inside facing portion of the housing may be of circular cross section and hence of a strict cylindrical shape.

It is also conceivable that the outside facing portion of the socket and inside facing portion of the housing feature an oval or elliptical cross-section. Other geometries, such like a quadratic or rectangular structure or flattened round or flattened oval cross sections are also conceivable and within the scope of certain aspects of the present invention. By means of providing mutually corresponding outside facing and inside facing portions or surfaces at the socket and at the housing, the flexible bag can be squeezed therebetween in a fluid tight way. Since the socket as well as the housing are of substantially rigid or stiff material, a long lasting and leak proof seal as well as a defined attachment of the flexible bag to the socket and/or to the housing can be provided.

Independent from the specific cross section of socket and/or receptacle or housing the flexible bag, in particular a rim thereof adjacent to the bag's opening, is squeezable in a fluid tight way between a radially outwardly facing portion of the socket and a correspondingly shaped or cooperating radially inwardly facing portion of the housing, in particular of its receptacle. In the present context the radial direction extends perpendicular to an imaginary surface normal of the flexible bag's opening's cross section. Hence, the radial direction lies in the plane or extends parallel to the plane defined by the bag's opening's cross section.

According to a further embodiment the socket comprises an annular groove to receive a correspondingly-shaped sealing ring. The annular groove may be of circular or oval or even of rectangular shape and extends all around the outside facing portion of the socket facing towards the inside facing portion of the flexible bag's sidewall and further facing towards the inside facing portion of the housing. The sealing ring, typically made of an elastomeric material, such like natural or synthetic rubber may comprise a kind of an O-ring. The sealing ring is configured and adapted to be assembled in the annular groove of the socket. By means of the elastically deformable sealing ring an improved seal between the flexible bag, socket and housing can be obtained. In addition, the sealing ring may also support and improve the mutual interconnection of the socket and the housing. By way of the sealing ring, a pull off force necessary to disassemble socket and housing may be increased.

In general there are various different ways to implement a mechanical connection and interaction of socket and housing. It is generally conceivable, that socket and housing are threadedly engaged. According to a further embodiment the housing is press fitted to the socket.

Hence, housing and socket may be mutually attached by way of a clamping or by means of a force closure. In typical embodiments the outside facing portion of the socket and the inside facing portion of the housing, which mutually engage, may comprise a somewhat conical shape so as to improve a press fitted mutual engagement. A press fitted engagement is particularly easy to implement and supports a rather intuitive and straight forward releasable assembly of socket and housing.

According to a further embodiment the flexible bag is sealingly press fitted with the housing by means of the sealing ring engaged with the housing. Typically, the sealing ring mounted in the annular groove of the socket is located inside the flexible bag. In an initial configuration prior to a mutual assembly of socket and housing, the outer diameter or outer dimensions of the sealing ring are slightly larger than the inner diameter or inner cross-section of the inside facing sidewall of the housing. It is then due to a compression and flexible deformation of the sealing ring, that the housing can be fitted over the socket, thereby clamping socket, housing, sealing ring and flexible bag located therebetween in a leak proof and sealed manner.

It is generally conceivable that the annular groove with the sealing ring is located on the inside facing portion of the housing, hence at an inside wall of the housing whereas the outside facing portion of the socket is substantially planar or even-shaped. Hence, it is generally conceivable, that one of outside facing portion of the socket and inside facing portion of the housing comprises an annular groove to receive a correspondingly-shaped sealing ring.

The sidewall of the flexible bag may be clamped and arranged between the sealing ring and the inside facing portion of the housing. In an alternative embodiment it is also conceivable, that the sidewall of the flexible bag is arranged between the annular groove and the sealing ring assembled in the annular groove. In this way, the flexible bag could be even preassembled to the socket even without the socket being in engagement with the housing. Hence, it is generally conceivable that the flexible bag is preassembled to the socket alone by means of the sealing ring assembled in the annular groove.

According to another embodiment the socket comprises a front face located inside the flexible bag. The fluid channel being in fluid communication with a cartridge fluid coupling extends into a front face's central portion. Hence, there is provided a hole in a central portion of the front face that serves as an inlet for the fluid channel or which belongs to the fluid channel. The fluid channel therefore ends and terminates in the front face's central portion. The liquid medicament located in the flexible bag sealed by the socket may be withdrawn through the fluid channel extending into the front face's central portion. By providing the fluid channel in a central portion of the front face, the fluid channel may be effectively protected against obstruction, which may occur due to a inwardly directed folding of the flexible bag during medicament withdrawal. By arranging the fluid channel in a central portion, it is located at a maximum distance from the sidewall of the flexible bag.

According to another embodiment the socket, in particular its front face comprises at least one fluid groove extending from a periphery of the front face into the fluid channel. The fluid groove provides an auxiliary fluid channel in the event that a portion of the front face should be covered or obstructed by an inwardly folded portion of the flexible bag. Moreover, since the at least one fluid groove extends into the centrally located fluid channel it is even conceivable that the fluid channel remains in fluid communication with the interior of the flexible bag even when obstructed by an inwardly folded portion of the flexible bag.

Typically, the size or cross-section of the at least one fluid groove is smaller than a typical bending or folding radius of the flexible bag so that the flexible bag's sidewall is generally unable to adapt the shape of the at least one fluid groove. Typically, the fluid groove comprises a semi-circular cross section. In typical embodiments there are located several fluid grooves in the front face of the socket. At least two of the fluid grooves or a plurality thereof merge and intersect in the central portion and hence overlap with the fluid channel. It is generally conceivable, that the fluid grooves extend radially outwardly with respect to the elongation of the fluid channel as an axis of symmetry.

In a further embodiment the housing of the disposable cartridge is substantially rigid. Typically, the housing comprises an injection molded plastic material that can be easily manufactured in a mass manufacturing process in a rather cost saving way.

By providing a rigid housing, the flexible bag can be effectively protected against environmental influences, in particular against pointed objects or sharp edges that may otherwise pierce or counteract the integrity of the flexible bag.

According to another embodiment the housing is substantially opaque and completely covers the flexible bag. By completely covering the flexible bag, the flexible bag can be effectively protected not only against external mechanical influences but also against electromagnetic radiation, such like radiation in the infrared, UV- or visible spectral range.

By having an opaque housing, the flexible bag can be kept in a dark or dim environment, which is beneficial for shelf life and long term stability of the medicament. Windows in the opaque housing may allow visual inspection of the drug reservoir. The windows maybe open or be filled or covered with transparent plastic material or glass.

In another embodiment the flexible bag is at least partially transparent. It is at least in sections transparent or partially transparent or it is completely transparent or partially transparent to allow visual inspection of its content. In this context partially transparent means that the flexible bag is penetrable by at least a portion of incident electromagnetic radiation, typically in the visible spectrum, to allow visual inspection of the medicament located therein.

In addition, the housing and in particular the rigid housing of the cartridge, which is typically substantially opaque, comprises at least one transparent window to allow visual inspection of the flexible bag's content. Apart from the window portion, hence outside the window the housing is substantially opaque. The window may form a through opening in a side wall or in a front or back face of the housing. The window may be covered or filled with a transparent material, e.g. with glass or a substantially transparent plastic material to hermetically seal the interior of the housing and to allow visual inspection of its content.

According to another embodiment the flexible bag comprises a predefined folding structure. For instance, the flexible bag may comprise a folding seam extending along a longitudinal elongation, in particular along a side wall of the flexible bag. The folding structure in form of a folding seam may be inherently provided by way of manufacturing of the flexible bag. Hence, the flexible bag may be manufactured and produced from two correspondingly-shaped plastic sheets or plastic foils that are welded together to form a folding seam. Typically, such a weld seam or folding seam may extend substantially along the elongation of the flexible bag, which may be of substantial cylindrical or flattened cylindrical form.

In other embodiments a folding structure may be also implemented by attaching some kind of folding means to the outer surface of the flexible bag. Here, a structurally reinforced or rigid folding structure may induce a well-defined folding behavior of the flexible bag. In effect, by means of the predefined folding structure it can be effectively prevented, that a sidewall portion of a collapsing flexible bag effectively obstructs the front face of the socket and hence the fluid channel and/or the at least one fluid groove in fluid communication with the fluid channel.

According to another embodiment the flexible bag comprises a support structure. The support structure may be located inside or outside the flexible bag. It may be directly attached to the inside or to the outside of the flexible bag or it may be attached and assembled to the socket when extending into the flexible bag. In particular, the support structure may extend into the flexible bag at a predefined distance to the bag's sidewall. It may comprise a post or a slab extending from the socket's front face into the flexible bag. By means of such a support structure, a rather undefined and arbitrary folding or collapsing behavior of the flexible bag can be prevented. Instead, the support structure supports and induces a well-defined folding and collapsing behavior of the flexible bag upon withdrawal of the medicament therefrom.

According to another embodiment the flexible bag is attached to the housing of the disposable cartridge at a predefined distance from the socket. In a typical implementation it is conceivable, that a remote portion of the flexible bag is mechanically connected to the housing. In this way, also an undefined collapsing or folding behavior of the flexible bag upon withdrawal of the medicament can be effectively prevented. It is generally conceivable, that the outer contour of a free end of the flexible bag located opposite the flexible bag's opening is for instance adhesively or otherwise attached to the inside of the housing. In this way it can be effectively prevented, that the particular free end of the flexible bag approaches the socket and its front face during medicament withdrawal. Hence, by means of attaching the flexible bag to the housing at a predefined distance from the socket a well-defined collapsing and folder behavior of the flexible bag can be enforced.

According to another embodiment at least one of the housing and the socket comprises a linear guiding to engage with at least one of a housing of a drug delivery device and a disposable injector. Likewise the disposable cartridge a disposable injector may also be releasably attachable or connectable with the drug delivery device, in particular with a housing of the drug delivery device. The disposable injector typically comprises a flexible tube and an injector fluid coupling to engage with the cartridge fluid coupling. In this way, the disposable cartridge and the disposable injector are mutually releasably engageable in a fluid transferring way.

It is the flexible tube of the disposable injector that may interact and cooperate with e.g. a feeder mechanism of the drug delivery device, typically implemented as a rotatable pump head. The injection needle of the injector is in fluid communication with the injector coupling by means of the flexible tube. In this way, the medicament initially located in the cartridge is directly transferred through the cartridge fluid coupling, the injector fluid coupling, into the flexible tube and hence towards the biological tissue, in which the injection needle is located during a dispensing procedure.

In a further embodiment the cartridge is configured and adapted to be attached to the housing of the drug delivery device or to the injector in an undeployed configuration. In this context undeployed configuration defines a fluidic decoupled configuration, in which injector fluid coupling and cartridge fluid coupling are decoupled or disengaged. In the undeployed configuration there is no fluid communication between the cartridge and the injector. The cartridge is particularly configured to be displaced relative to the injector and/or relative to the housing of the drug delivery device from the undeployed configuration or undeployed position into a deployed configuration and hence into a deployed position. In the deployed position the cartridge fluid coupling is in fluid communication with the injector fluid coupling. Then, the cartridge and hence its flexible bag is in fluid communication with the injector and hence with the injection needle thereof. Mutual displacement of cartridge and injector relative to each other between the deployed and undeployed configuration may be exclusively established and controlled by the drug delivery device.

In another aspect, a drug delivery device for dispensing of a liquid medicament, typically by way of injection, comprises a housing having at least one feeder member, such like a rotatable pump head. The drug delivery device may be implemented as a peristaltic pump or some other kind of injector. The drug delivery device further comprises a disposable injector that has an injection needle, a flexible tube and injector fluid coupling. The injection needle is in permanent fluid communication with the fluid coupling via the flexible tube. Upon engaging of the injector fluid coupling with a corresponding cartridge fluid coupling a direct fluid communication between disposable cartridge and disposable injector can be established. By way of a mechanical engagement and interaction between the flexible tube and the feeder member a well-defined fluid flow of medicament can be provided.

According to a further embodiment the disposable cartridge and the disposable injector are releasably engageable to establish a fluid communication by means of the fastener pivotally attached to the housing. Typically, the fastener is operable to releasably fix and to liberate at least one of disposable cartridge and disposable injector. In addition, the fastener is selectively engageable with only one of disposable cartridge and disposable injector so as to induce a displacement of one of disposable cartridge and disposable injector relative to the other one of disposable cartridge and disposable injector. In this way, an undeployed configuration of disposable cartridge and disposable injector can be transferred to a deployed configuration and eventually even vice versa, wherein the respective transfer is exclusively driven and controlled by pivoting the fastener of the drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following an embodiment of the disposable delivery assembly in connection with a drug delivery device is described in more detail by making reference to the drawings, in which:

FIG. 1 is a perspective view of a first embodiment of the disposable cartridge,

FIG. 2 shows an exploded view of the cartridge according to FIG. 1,

DETAILED DESCRIPTION

Figure 3:
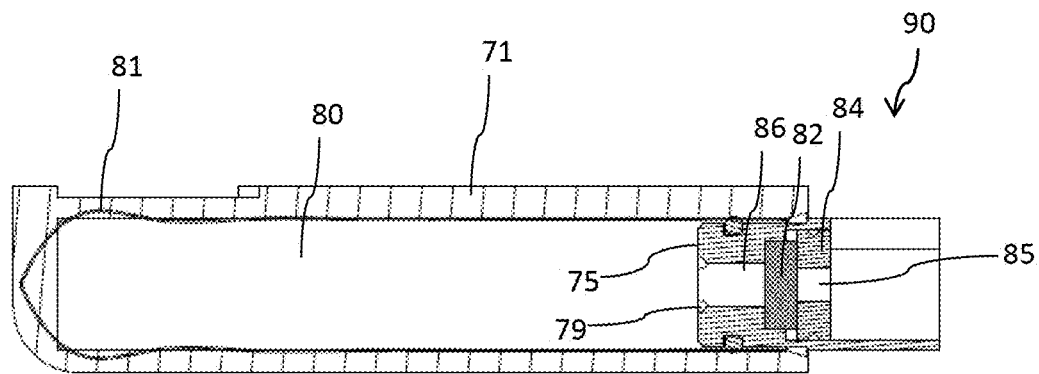
FIG. 3 shows the cartridge according to FIG. 1 in longitudinal cross-section.

The disposable cartridge 70 as shown in FIG. 1 comprises a base 74 featuring a socket 76 and further having a housing 71 to engage with the base 74, in particular with its socket 76. The cartridge 70 further comprises a reservoir 80 to receive a liquid medicament. The reservoir comprises a flexible bag 81 featuring an opening 81a. Adjacent to the opening 81a the flexible bag 81 comprises a sidewall 81b by way of which the flexible bag 81 is attached to the socket 76. As becomes apparent from the cross-section according to FIG. 3, the socket 76 of the cartridge's 70 base 74 is inserted into the opening 81a such that the interior of the sidewall 81b gets in direct contact with an outside portion 76a of the socket 76.

The cross-section of the flexible bag's 81 opening 81a is completely filled of obstructed by the socket 76. Typically, the sidewall 81b is sealingly engaged with the socket 76. In this way, the flexible bag 81 is effectively sealed by the socket 76. Additionally, the flexible bag 81 is mounted to the socket 76 and is therefore mechanically fastened to and inside the cartridge 70 by way of the mechanical engagement with the socket 76.

As further illustrated in FIG. 3, the socket comprises a fluid channel 86 extending into a front face 75 of the socket 76, which front face 75 is located inside the flexible bag 81 and hence inside the reservoir 80. The disposable cartridge 70 further comprises a cartridge fluid coupling 90 by way of which fluid transferring access to the interior of the reservoir 80 can be provided. The cartridge fluid coupling 90 is typically provided with a sealing disc 82 or by some other kind of sealing member completely obstructing an outlet of the fluid channel 86. In the embodiment as shown in FIG. 3, the sealing disc 82, typically comprising a flexible and pierceable member is fixed to the base 74 by means of an insert 84, which axially abuts the sealing disc 82.

In the present context, axial direction denotes the direction of the main elongation of the cartridge 70. Here, elongation of the fluid channel and the fluid flow direction defined by the fluid channel 86 substantially coincide with the axial direction. The insert 84 may be press fitted in a correspondingly-shaped receptacle of the base 74. Alternatively, the insert 84 may be threadedly engaged with the base 74 to axially clamp and to axially fix the sealing disc 82 in a sealing position and sealing configuration.

Figure 10:
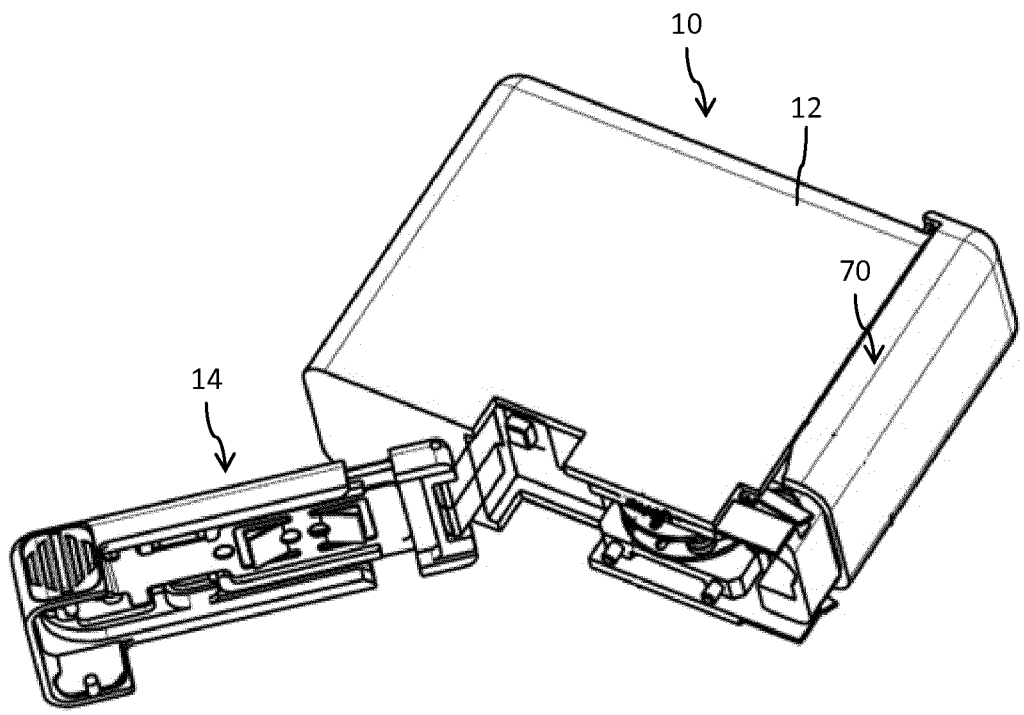
FIG. 10 shows the drug delivery device according to FIG. 9 with a cartridge assembled thereto.

The sealing disc 82, effectively serving as a pierceable septum may be pierced or penetrated by a tipped cannula 68a of an injector 60 as shown in FIG. 10.

Figure 4:
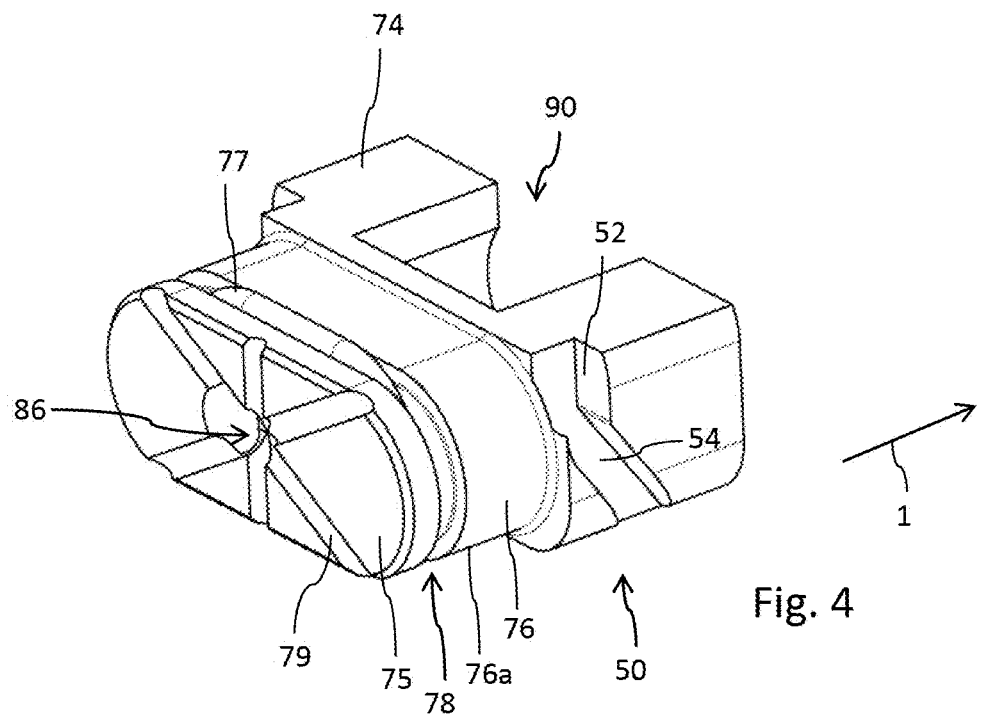
FIG. 4 shows an isolated view of the cartridge's socket.

The enlarged perspective view according to FIG. 4 shows the base 74 of the disposable cartridge 70. The base 74 with the axially extending socket 76 comprises a substantially planar-shaped front face 75 at that end of the socket 76 which is located inside the reservoir 80. The front face 75 comprises a central opening that coincides with the fluid channel 86. In addition, the front face 75 comprises several fluid grooves 79 that extend from a periphery of the front face 75 towards and into the centrally located fluid channel 86. The fluid grooves 79 substantially extend radially outwardly given that the front face 75 and hence the socket 76 feature an oval, elliptic or circular shape.

At a predefined distance from the front face 75 the socket 76 further comprises a circumferentially extending groove 78 to receive an annular or a closed sealing ring 77. The sealing ring 77 typically comprises an elastomeric material and effectively serves as or comprises an O-ring, which at least partially protrudes from the outside facing sidewall portion 76a of the socket 76 when assembled in the groove 78. The sidewall 81b of the flexible bag 81 extending over the socket 76 and over the sealing ring 77, which located inside the groove 78, is radially squeezed between the sealing ring 77 and an inside facing portion 71b of a cartridge's 70 housing 71.

Figure 5:
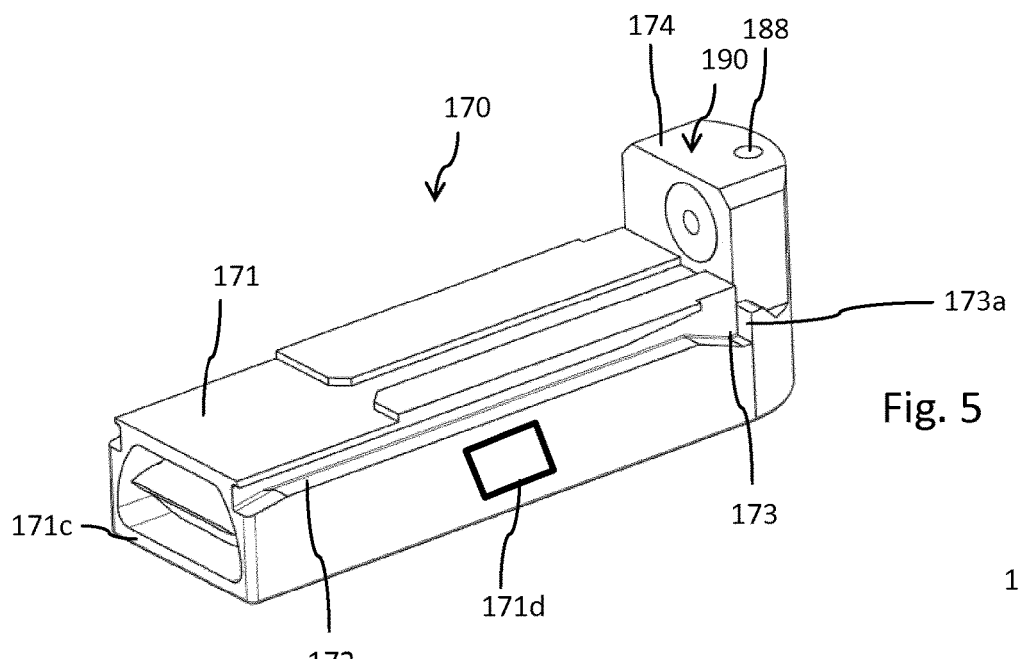
FIG. 5 shows another embodiment of the disposable cartridge in a perspective view.
Figure 6:
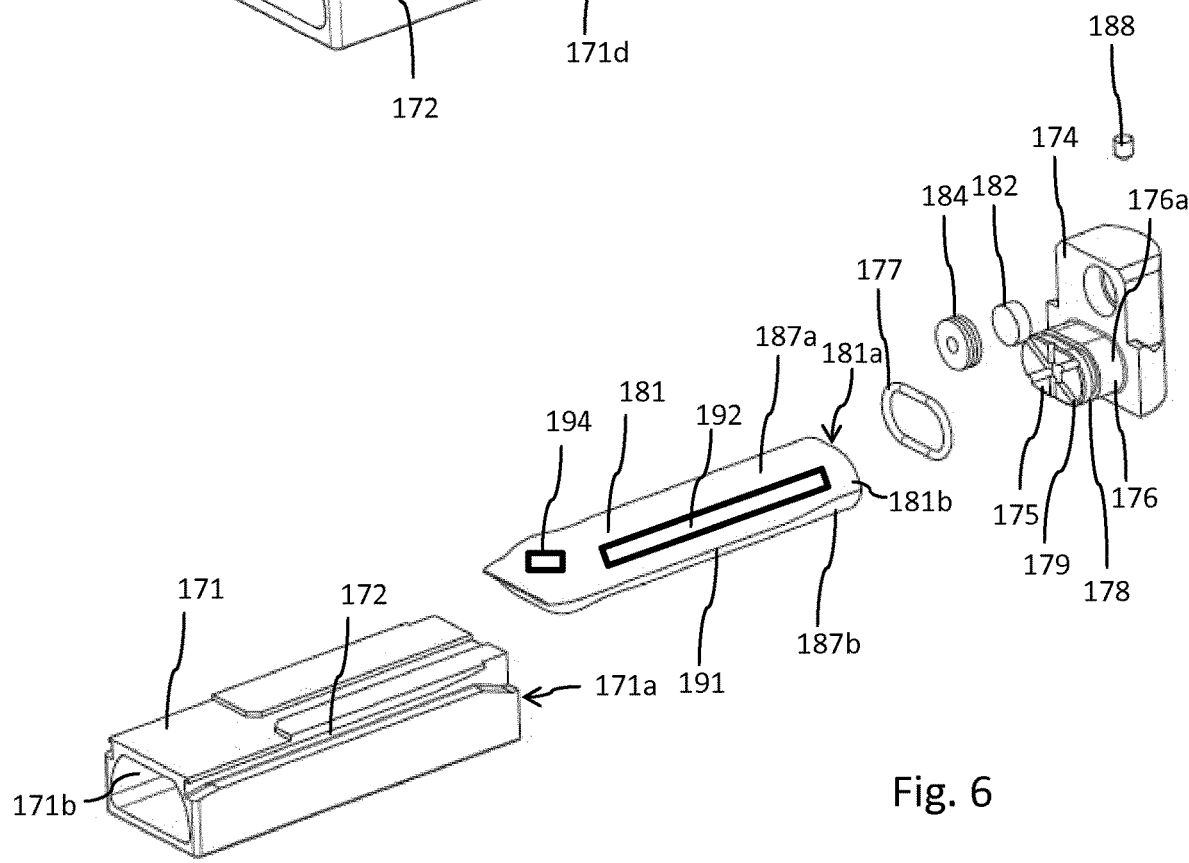
FIG. 6 is an exploded view of the cartridge according to FIG. 5.

The housing 71 provides a protective sheath for the reservoir 80 and hence for the flexible bag 81. It extends all over the outer circumference of the flexible bag 81 and provides a mechanically protective means for the flexible bag 81, especially against sharp edges or tipped objects. Furthermore, the housing 71 is opaque so as to provide protection against electromagnetic radiation for the medicament located in the flexible bag, which bag may be at last in sections transparent. Typically, the entire housing is of a rigid and opaque plastic material. Nevertheless, the housing 71, 171, as illustrated in FIGS. 2 and 5 may also comprise an aperture, through opening or a window 71d, 171d that may be covered of filled by a transparent material in order to allow a visual inspection of the content of the flexible bag 81. In particular, diametrically oppositely located side wall portions of the housing 71, 171 may each comprise a window 71d,171d to improve visual inspection of the bag's 81 content, i.e. the medicament.

The housing 71 comprises a receptacle 71a as illustrated in FIG. 2 and an inside facing sidewall portion 71b to mechanically engage with the outside facing portion 76a of the socket 76. In the present embodiment, wherein the socket 76 and the receptacle 71a are of substantially oval or elliptic shape the socket 76 and hence the base 74 and the housing 71 are mechanically mutually engageable by way of a press fit engagement or by some other type of force closure. In other embodiments, wherein receptacle 71a and socket 76 may be of strict cylindrical geometry it is also conceivable that receptacle 71 and socket 76 are threadedly engaged, thereby enabling a well-defined disassembly of housing 71 and base 74.

The fluid grooves 79 provided in the front face 75 of the socket 76 are in permanent fluid communication with the fluid channel 86. In the event that the flexible bag 81, in particular a sidewall portion 81b thereof should collapse in such a way that a portion of the front face 75 is covered with a sidewall portion 81b unobstructed portions of fluid grooves 79 still provide a bypass so that the liquid medicament can be further withdrawn from the flexible bag 81. The flexible bag 81 may inherently comprise a folding structure 91. As indicated in FIG. 2, the flexible bag 81 may be formed of an upper portion 87a and a lower portion 87b of sheet or foil that are welded together along a longitudinally or axially extending weld seam that forms a predefined folding structure 91 for the flexible bag 81.

The predefined folding structure may be formed by structurally connecting the upper portion 87a of the flexible bag 81 with the correspondingly-shaped lower portion 87b of the flexible bag 81. During withdrawal of the liquid medicament from the flexible bag 81 through the fluid channel 86 upper and lower portion 87a and 87b may collapse in such a way, that upper and lower portion 87a, 87b form a substantially planar or even shaped collapsed structure. The folding structure 91 that may be formed by a weld seam interconnecting upper portion 87a and lower portion 87b may effectively prevent collapsing of the flexible bag 81 in axial direction, i.e. towards the base 74.

Alternatively or additionally the flexible bag 81 may be engaged with or provided with a support structure 92 extending either inside or outside the flexible bag 81. The support structure 92 may be directly attached to the flexible bag's 81 sidewall 81b. It is also conceivable, that the support structure 92 extends like a post or like a slab substantially perpendicular from the front face 75 of the socket 76 of the base 74 into the interior of the flexible bag 81. In this way, the support structure 92 comprising a substantially stiff and inflexible object may be initially located at a distance from the flexible bag's 81 sidewall 81b. As soon as the flexible bag 81 collapses during withdrawal of a medicament therefrom the support structure 92 effectively counteracts an axial displacement of the flexible bag's 81 sidewall 81b towards the front face 75 and towards the socket 76.

It is also conceivable, that at least one of upper and lower portions 87a, 87b comprises a fixing portion 94 to fix or to attach the flexible bag 81 to an inside facing portion of the housing 71. For instance, the fixing portion 94 may be adhesively attached to the housing 71 at a predefined distance from the front face 75 and hence from the socket 76 of the base 74. By at least punctually adhering or fixing the flexible bag 81 to the housing 71, an uncontrolled or arbitrary collapsing behavior of the flexible bag 81 can be effectively prevented.

By means of the fixing portion 94, the flexible bag 81 is attachable to the housing 71 at a predefined distance from the socket 76.

Figure 9:
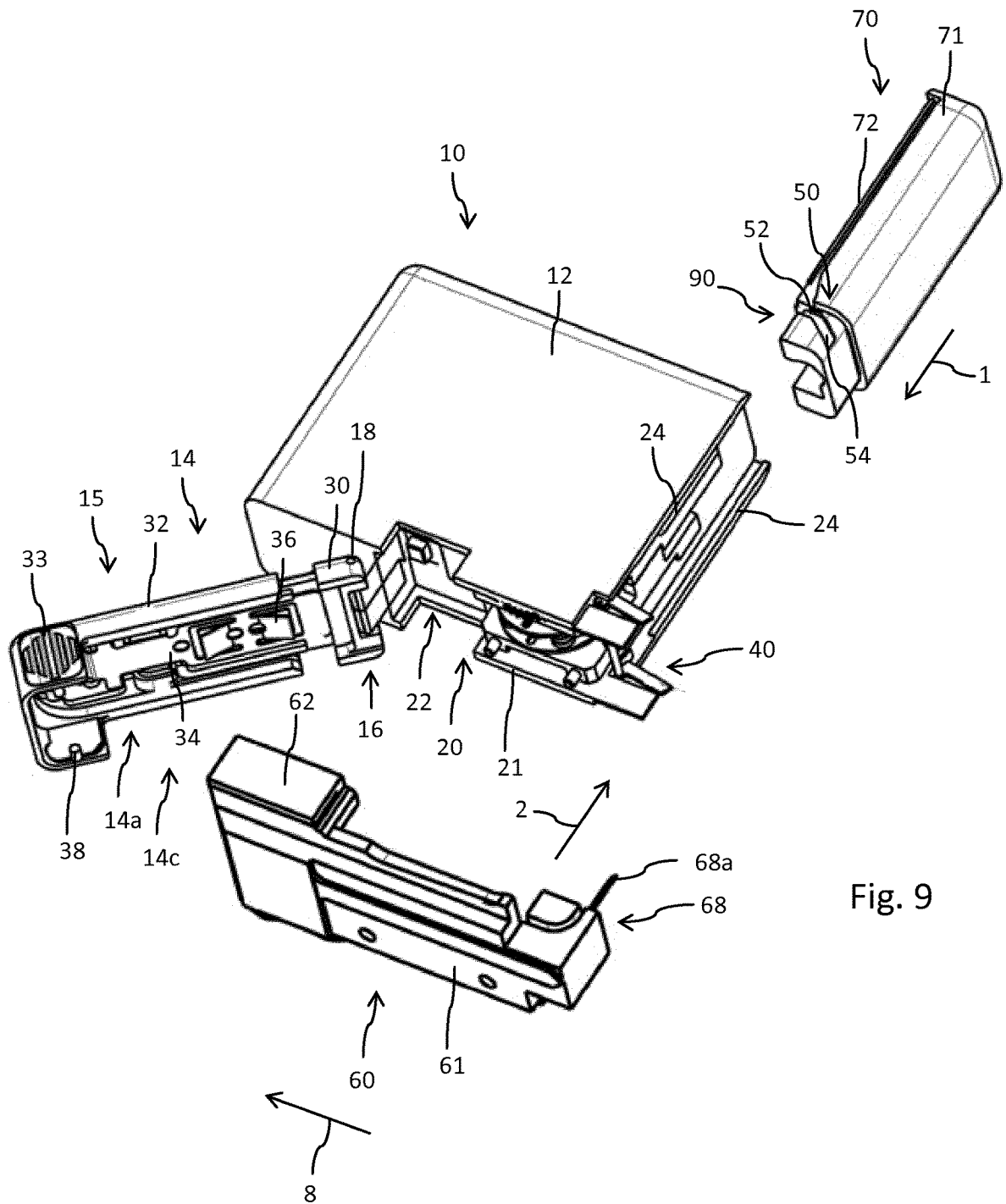
FIG. 9 is illustrative of the assembly of the cartridge according to FIG. 1 to a drug delivery device.
Figure 11:
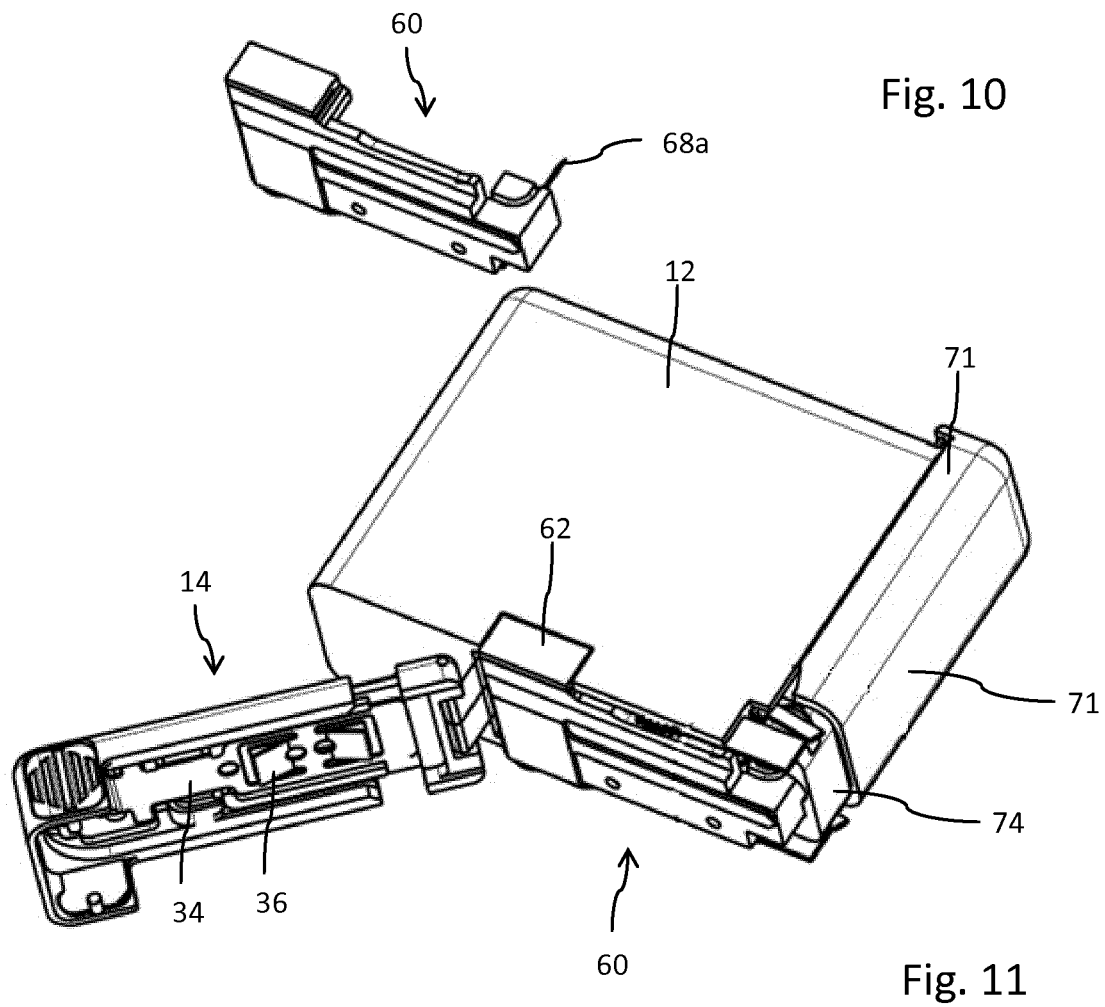
FIG. 11 shows the drug delivery device according to FIG. 10 with the disposable injector assembled in a receptacle of the drug delivery device.

By arranging the flexible bag 81 in a rigid housing 71 the cartridge 70 itself may become a portion of the housing of a drug delivery device as for instance illustrated in FIGS. 9-11. The cartridge 70 with its housing 71 may be integrated into the housing of a drug delivery device 10. By protecting the flexible bag 81 by means of a housing 71 completely receiving the flexible bag 81, the flexible bag 81 itself can be provided with a decreased inherent rigidity and may therefore provide less resistance in regard of flexible deformation during withdrawal of the medicament. Hence, the suction capability of a pump or of a feeding mechanism of the drug delivery device 10 can be reduced, thereby reducing energy consumption and extending battery lifetime when implemented as a mobile drug delivery device.

In the sequence of FIGS. 9-13 engagement of the cartridge 70 with a drug delivery device 10 is illustrated and described below.

Figure 12:
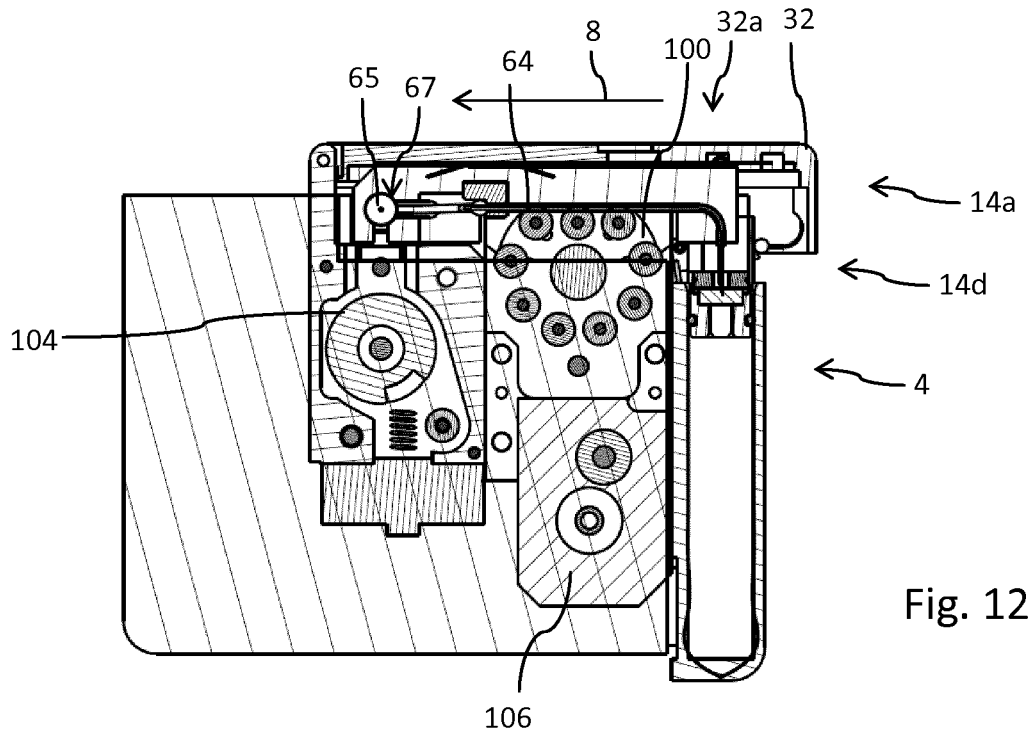
FIG. 12 shows cartridge and injector of the drug delivery device according to FIGS. 9-11 in an undeployed configuration.
Figure 13:
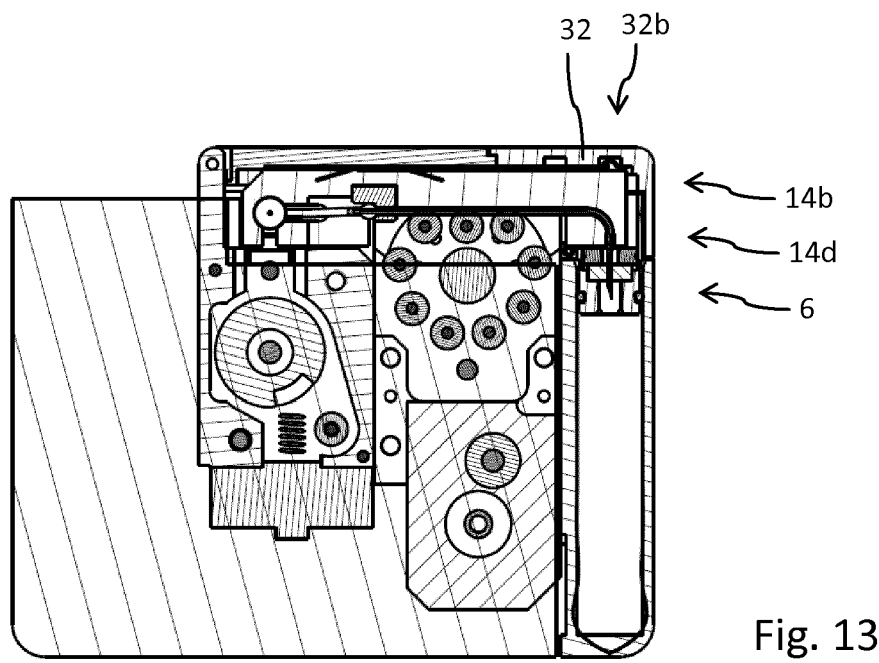
FIG. 13 shows the drug delivery device according to FIGS. 9-12 with disposable cartridge and injector in a deployed configuration.

The drug delivery device 10 as it is illustrated in FIGS. 9-13 comprises a housing 10 featuring a receptacle 20 which is closeable by a fastener 14 that serves as a lid 15 for the receptacle 20. The fastener 14 is pivot mounted to the housing 12 by means of a hinge 16. Consequently, the fastener 14 is pivotable between a closed configuration 14d as shown in FIGS. 12 and 13 and an opened configuration 14c as illustrated in FIG. 9 for instance. In the opened configuration 14c, the receptacle 20 is accessible from outside to insert a disposable injector 60. The injector 60 is insertable into the receptacle 20 along an insert direction 2 as illustrated in FIG. 1.

The drug delivery device 10, typically implemented as a peristaltic pump, is designed to releasably engage with a disposable injector 60 and with a disposable cartridge 70. The disposable injector 60 as shown in FIG. 10 comprises a base 61. The base features a track through which a flexible tube is guided. In the region of the track the feeder member 100 or the pump head of the drug delivery device 10 engages with the flexible tube. The flexible tube 64 is squeezable by the feeder member 100 in order to transport the liquid medicament from the reservoir 80 of the cartridge 70 towards an injection needle of the injector 60.

The injection needle, which is not particularly illustrated also belongs to the injector 60. It may be slideably received in a conduct of the injector 60. Typically, when arranged in the receptacle 20 of the drug delivery device 10 that side face of the injector 60 featuring the outlet for the injection needle forms an integral component of the outer surface or housing 12 of the drug delivery device 10. In typical application scenarios, the drug delivery device 10 is e.g. adhesively attached to the skin of a patient. Upon activation of the injector 60, hence upon activation of the drug delivery device 10 the injection needle is automatically positioned into the extended position thereby piercing or penetrating dermal tissue for transdermal or subcutaneous injection of the liquid medicament.

Opposite the injection needle the injector 60 comprises an injector fluid coupling 68, presently in form of a hollow but tipped cannula 68a. As becomes apparent from FIG. 10, the injector fluid coupling 68 extends from a sidewall of the injector's base 61. The tipped injector fluid coupling 68 serves to penetrate and to pierce a cartridge fluid coupling 90 of the cartridge 70 as for instance illustrated in FIG. 13. As already explained above the cartridge fluid coupling 90 comprises the pierceable seal 82 which is penetrated by the injector fluid coupling 68 when injector 60 and cartridge 70 arrive at the deployed configuration 6 as shown in FIG. 13.

As becomes apparent from FIG. 9 disposable injector 60 and disposable cartridge 70 are separately releasably engageable with the housing 12 of the drug delivery device 10. For this purpose the cartridge 70 comprises a linear guiding 72, e.g. in form of a longitudinal groove at its longitudinally extending housing 71 that engages with a correspondingly-shaped guide section 24 at a sidewall portion of the housing 12 as illustrated in FIG. 1. By means of the linear guiding 72 of the cartridge 70 engaging with the housing's guide section 24, the cartridge 70 is displaceable along the housing 12 of the drug delivery device 10 along a deploy direction 1.

The injector 60 extends substantially perpendicular to the elongation of the cartridge 70 and is configured to be positioned in the receptacle 20 located at an adjacent sidewall portion of the drug delivery device's 10 housing 12. The injector 60 having a base 61 features a mating structure 62 that mates with a recessed structure 22 of the housing 20, hence of a sidewall portion 21 of said housing 20. In this way, the mating structure 62 may be flush mounted to the outside facing portion of the housing 12. The mating structure 62 of the injector 60 may form a component of the housing 12 and may contribute to the outer appearance of the drug delivery device 10 as becomes apparent from FIG. 11 for instance.

As it is apparent from FIG. 1, the injector fluid coupling 68 in form of a tipped cannula 68a extends substantially perpendicular to the elongation of the injector 60. In particular, the injector fluid coupling 68 and its tipped cannula 68a extend in deploy direction 1 so as to engage with the cartridge fluid coupling 90 of the cartridge 70.

The cartridge 70 is attachable and displaceable along the deploy direction 1 along the side face of the housing 12 being equipped with the guide sections 24. Here, the cartridge 70 is displaceable in deploy direction 1 until it engages with a pivotable stopper 40. The pivotable stopper 40 is pivotable between a stop configuration and a release configuration In the stop configuration a stop portion 43 of the stopper 40 directly abuts with a stop face 48 of the housing 71 of the cartridge 70 thereby inhibiting a further displacement of the cartridge beyond the undeployed position 4, in which the cartridge fluid coupling 90 and the injector fluid coupling 68 are disconnected. Further displacement of the cartridge 70 in deploy direction 1 and in order to establish a fluid communication between the cartridge 70 and the injector 60 requires pivoting of the stopper 40, e.g. in a counter-clockwise direction. Such a pivoting may be induced by closing of the fastener 14 hence by pivoting the fastener 14 into a closed configuration 14d as for instance shown in FIG. 13.

In the closed configuration 14d the inwardly extending guiding pins 38 located at an inside portion of the fastener 14 engage with the beveled ends of the stopper 40. Typically, the guiding pins 38 extend inwardly from a slider 32 of the fastener 14, which slider 32 being slidably fastened to a base portion 30 of the fastener 14 and which base portion 30 being pivotably attached to the housing 12. Engagement of the guiding pins 38 with the stopper 40 may already take place when the fastener 14 reaches the closed configuration 14*d*, in which the receptacle 20 receiving the injector 60 is substantially closed.

As illustrated further the base 74 of the cartridge 70 comprises a sliding groove 50 serving as a coulisse for the guiding pins 38 of the fastener 14. As indicated in FIG. 9 the sliding groove 50 comprises a beveled portion 54 extending at a particular angle with regard to the deploy direction 1. The beveled portion 54 then merges into a substantially vertically extending locking portion 52 which extends substantially perpendicular to the deploy direction 1 but substantially parallel to a displacement direction 8 along which a portion of the fastener 14, in particular a slider 32 is displaceable between an extended position 32*a* as shown in FIG. 12 and a retracted position 32*b* as shown in FIG. 13.

As it is apparent from FIG. 1, the beveled portion 54 of the sliding groove 50 of the cartridge's 70 base 74 extends towards the deploy direction 1 in opposite direction to the locking direction 8. In the undeployed configuration 4 as shown in FIG. 12 the guiding pins 38 are in a position just to enter the beveled portion 54 of the sliding groove 50 that faces away from the locking portion 52. Upon entering the sliding groove 50 by a displacement of the fastener 14, hence by a displacement of the fastener's 14 slider 32 in locking direction 8, an initial displacement of the guiding pins 38 in locking direction 8 initially serves to pivot the stopper 40 towards the release configuration. Thereafter, a further sliding displacement of the guiding pins 38 in locking direction 8 leads to a forced advancing of the guiding pins 38 along the beveled portion 54 of the sliding groove 50 until the guiding pins 38 reach the locking portion 52 thereof extending substantially parallel to the locking direction 8.

Once the medicament contained in the reservoir 80 has been withdrawn thus requiring a replacement of the cartridge 70 the slider 32 may be displaced in a direction opposite to the locking direction 8, typically by means of the ripples 33 provided at the outer surface of the free end of the slider 32. Since the guiding pins 38 remain in permanent engagement with the sliding groove 50 of the cartridge's 70 base 74, a reverse displacement of the slider 32 of the fastener 14 into the release configuration 14*a* also leads to a reverse motion and displacement of the cartridge 70 in a direction opposite the deploy direction 1.

With the present embodiment it is of particular benefit, that the fastener 14 with its slider 32 serves as a lid 15 to cover and to close the receptacle 20 of the drug delivery device 10 in which the injector 60 is releasably received. Interlocking of the slider 32 and hence of the fastener is obtained through the interaction of the guiding pins 38 of the slider 32 with the sliding groove 50 of the cartridge 70. In the closed configuration 14*d* and in the locking configuration 14*b* as for instance shown in FIG. 13, the slider 32 and hence the fastener 14 is interlocked with and to the housing 12 in the locking configuration 14*b* through its guiding pin's 38 interaction with the sliding groove's 50 locking portion 52 of the cartridge 70.

The fastener 14 not only provides a twofold function by fixing the injector 60 to the housing 12 and by displacing the cartridge 70 between the undeployed configuration 4 and the deployed configuration 6 but through its interaction with the sliding groove 50 also serves to lock the fastener 14 and hence the lid 15 in the locking configuration 14*d*, in which the slider 32 is substantially flush with the housing 71 of the cartridge as illustrated in FIG. 13. Here, as soon as either the housing 71 of the cartridge 70 may extend or protrude from an adjacent housing portion 12 or in the event that the slider 32 extends or protrudes from the outer circumference of the adjacently located cartridge housing 71 a clear and unequivocal indication is given to a user, that the drug delivery device 10 is not correctly assembled or that the drug delivery device is currently under maintenance. In this way, a haptic feedback can be given to a user, whether cartridge 70 and injector 60 are correctly mounted to the housing 12.

Deployment of injector 60 and cartridge 70, hence establishing of a fluid transferring interconnection of injector 60 and cartridge 70 may only take place through interaction with the fastener 14 of the drug delivery device 10. In a reverse order also a disconnecting and decoupling of disposable cartridge 70 and disposable injector 60 can be provided simply by opening of the lid 15. For this the interlock between the fastener 14 and the cartridge has to be suspended by means of shifting the slider 32 from the locking configuration 14*b* towards the release configuration 14*a*. Here, the engagement of the sliding groove 50 with the guiding pins 38 induces a displacement of the cartridge 60 towards its undeployed position 4, hence in a direction opposite the deploy direction 1. Once the guiding pins 38 leave the sliding groove 50 the fastener 14 will be automatically lifted by a predefined angle due to the wings 36 of the spring 34 applying pressure to the upper surface of the injector 60 as will be explained below. This is a clear indication to the user, that the drug delivery device 10 is in a maintenance mode.

Due to the automated disconnection of cartridge 70 and injector 60 upon or prior to an opening of the lid 15 contamination of the environment by droplets of the medicament rinsing out of the injection needle 65 can be effectively avoided. Also here, it is conceivable that cartridge 70 and injector 60 comprises mutually corresponding tamper proof members, which serve to avoid reconnection or redeployment of cartridge 70 and injector 60 once they have been transferred from the deployed configuration 6 back into the undeployed configuration 4.

Figure 13A:
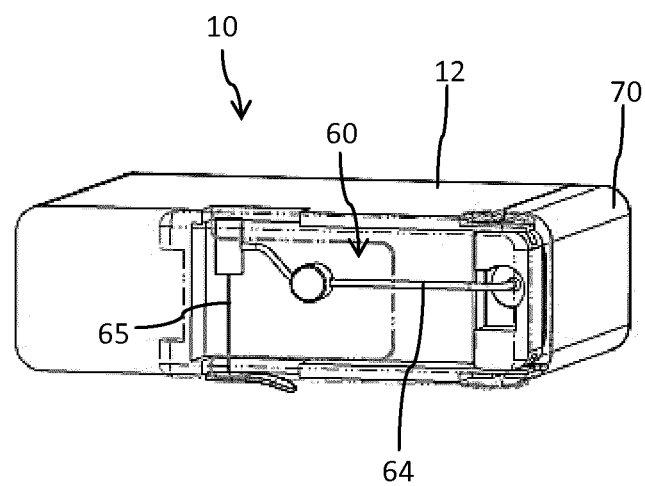
FIG. 13a shows the drug delivery device according to FIGS. 9 to 12 in a perspective view.
Figure 13B:
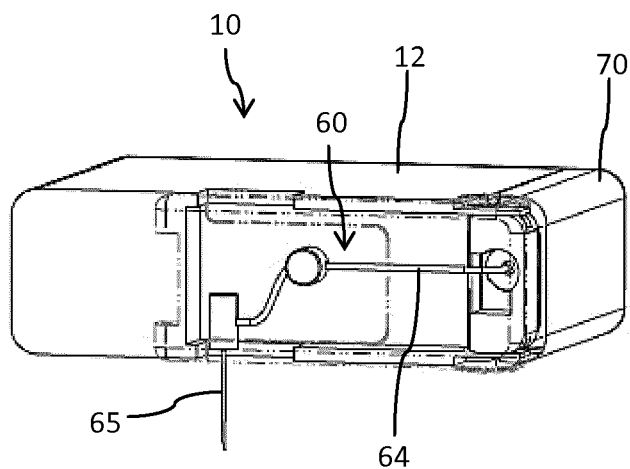
FIG. 13b shows the drug delivery device of FIG. 13a with an exposed injection needle.

The drug delivery device 10 as for instance illustrated in FIG. 12 is designed and implemented as a peristaltic pump. It comprises a feeder member 100, presently in form of a rotatable pump head that engages with the flexible tube 64 in order to squeeze the same for drug delivery. In addition, the drug delivery device 10 comprises an energy source, typically in form of an electric battery (not illustrated). Moreover, it comprises an injection drive 104 by way of which the injection needle 65 can be displaced along the conduct 67. By means of the injection drive 104 the injection needle 65 can be displaced from an initial position into an extended position as shown in FIGS. 13*a* and 13*b*. In the same way the injection drive 104 may serve to retract the extended injection needle 65. Additionally, the peristaltic pump 10 comprises a delivery drive 106 in order to set the pump head, hence the feeder member 100 in rotation during and for drug delivery.

In FIGS. 5-8 another embodiment of a cartridge 170 is illustrated. Unless otherwise described or specified the cartridge 170 features a similar structure compared to the cartridge 70. Similar or like components of cartridge 170 are therefore denoted with identical reference numerals increased by 100.

Figure 7:
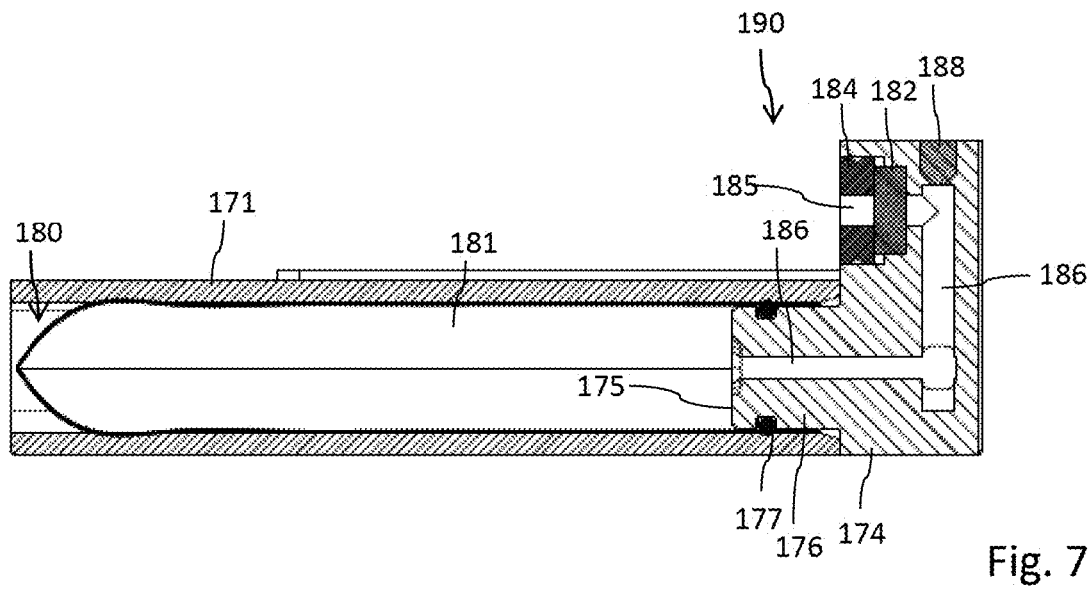
FIG. 7 is a longitudinal cross-section through the cartridge according to FIG. 5.
Figure 8:
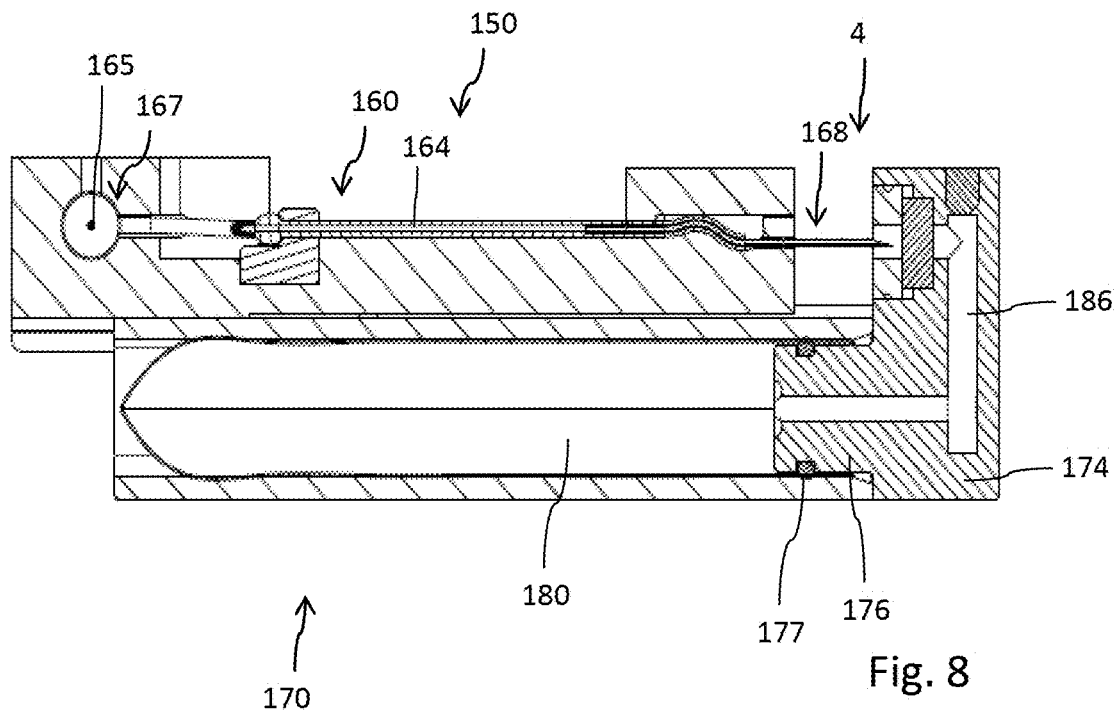
FIG. 8 is a longitudinal cross-section through the cartridge according to FIG. 5 connected to a disposable injector in an undeployed configuration.

The cartridge 170 distinguishes from cartridge 70 in regard of the geometry of the base 174 and the fluid channel 186 located therein. The fluid channel 186 extends from a middle portion of the socket's 176 front face 175 into the base 174. As shown in FIGS. 7 and 8 the fluid channel 186 extends substantially horizontal and then vertically upwardly before it merges and extends into an outlet section that is sealed by the pierceable seal 182. The outlet section forming the cartridge fluid coupling 190 is arranged and oriented substantially parallel to the lower portion of the fluid channel 186 which is in extension of the reservoir 180 and parallel to a linear guiding 172. In this way, the pierceable seal 182 can be pierced and penetrated by the injector fluid coupling 168, hence by its cannula 168*a*. At an upper portion of the vertical segment of the fluid channel 186 there is located a closure 188 that may serve as a ventilation. The closure 188 may be removable to eventually refill the reservoir 180 by a refill- or retail service. The insert 184 that keeps the pierceable seal 182 in position may comprise an outer thread to engage with an inner thread of a corresponding opening of the base 174. Alternatively, the insert 184 is press fitted or squeezed in the base 174.

In particular, the cartridge 170 is adapted to be preassembled with a disposable injector 160 as shown in FIG. 8 to form a disposable delivery assembly 150. The interaction and use of a disposable delivery assembly 150 as schematically illustrated in FIG. 8 with another embodiment of a drug delivery device 110 becomes apparent from the series of FIGS. 14-17 and as will be explained below.

Figure 14:
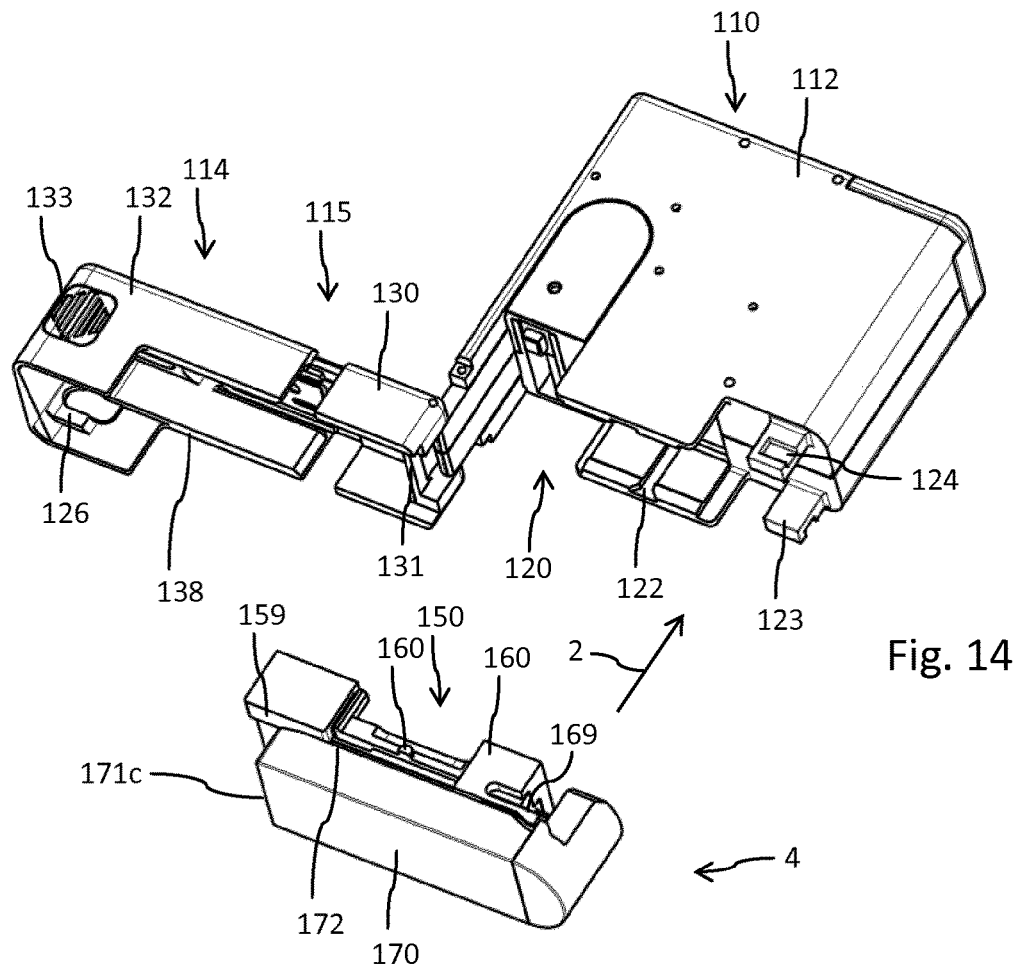
FIG. 14 shows an initial configuration of another drug delivery device to cooperate with a disposable delivery assembly equipped with a cartridge according to FIG. 5.

The housing 171 of the cartridge 170 also comprises a linear guiding 172 in form of a longitudinal groove that cooperates and engages with a guide section 159 of the injector 160 as illustrated in FIG. 14. In this way, cartridge 170 and injector 160 can be mechanically connected in a well-defined way but undeployed configuration 4, in which the cannula 168*a* of the injector 160 does not yet penetrate or pierce the pierceable seal 182 of the cartridge 170. The linear guiding 172 further supports and defines a mutual linear and straight displacement of the disposable injector 160 relative to the cartridge 170. Hence, the cartridge 170 may be displaced along the linear guiding 172 with regard to the injector 160 being fixed in the housing 120.

In an initial and undeployed configuration 4 as illustrated in FIGS. 5 and 14, the injector 160 and the cartridge 170 are mutually assembled in such a way, that the stop member 169 protruding from a sidewall portion of the injector 160 is in abutment with a corresponding stop face 173*a* of the cartridge 170. The linear guiding 172 provided as a linearly and rather straight extending groove at a sidewall portion of the housing 171 features a recess 173 formed by a beveled portion of the linear guiding 172.

Consequently, when reaching the undeployed configuration 4 as shown in FIG. 14, the flexible deformable stop member 169 enters the beveled recess 173 of the linear guiding 172 thereby preventing to displace the cartridge 170 relative to the injector 160 to arrive at the deployed configuration 6.

A sidewall portion 138 of the lid-shaped fastener 14 serves as a decoupler for the stop member 169. Hence, when reaching a closed configuration 14*d* the pivotable or flexible deformable stop member 69 is pressed downwards so to leave the recess 173 and the stop face 173*a* of the cartridge 170, thereby allowing that the cartridge 170 can be further displaced towards the deploy direction 1 until it reaches a deployed configuration.

By inserting the delivery assembly 150 an outwardly-extending protrusion 162 into a recessed structure 122 of the receptacle 120, only the disposable injector 160 thereof can be secured and fixed to the housing 112 of the drug delivery device 110 in regard to the deploy direction 1, which in the present embodiment extends substantially perpendicular to the insert direction 2.

Figure 15:
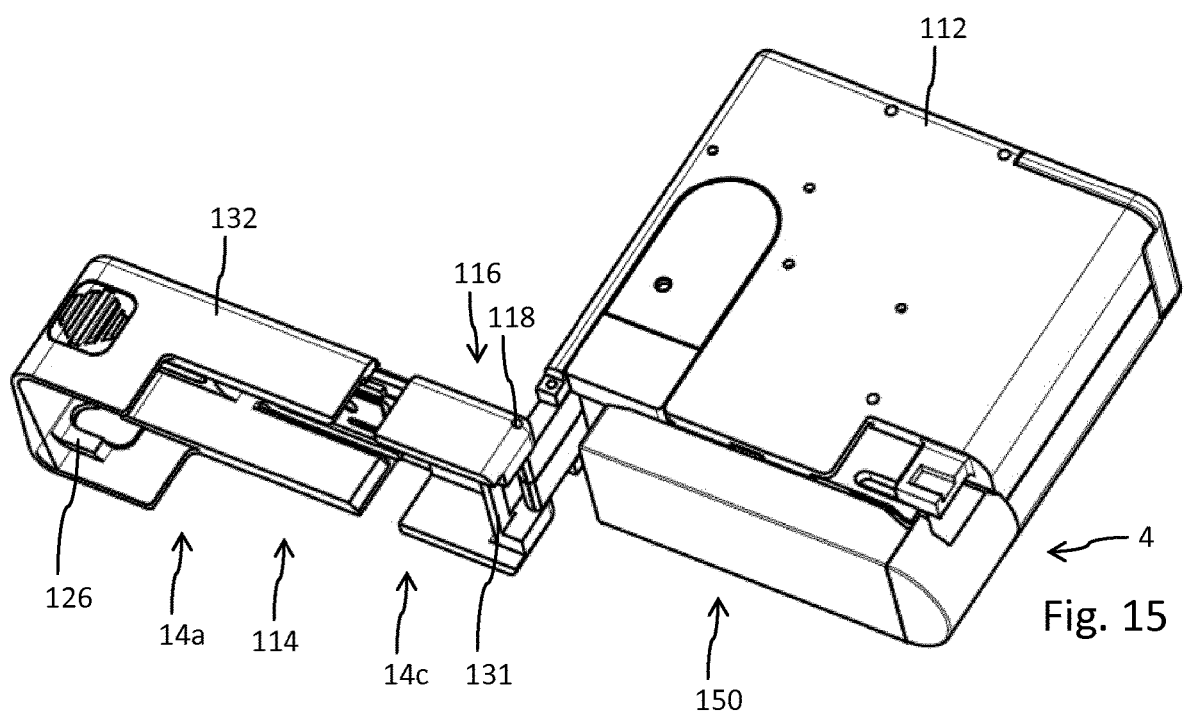
FIG. 15 shows the drug delivery device with the disposable delivery assembly
Figure 16:
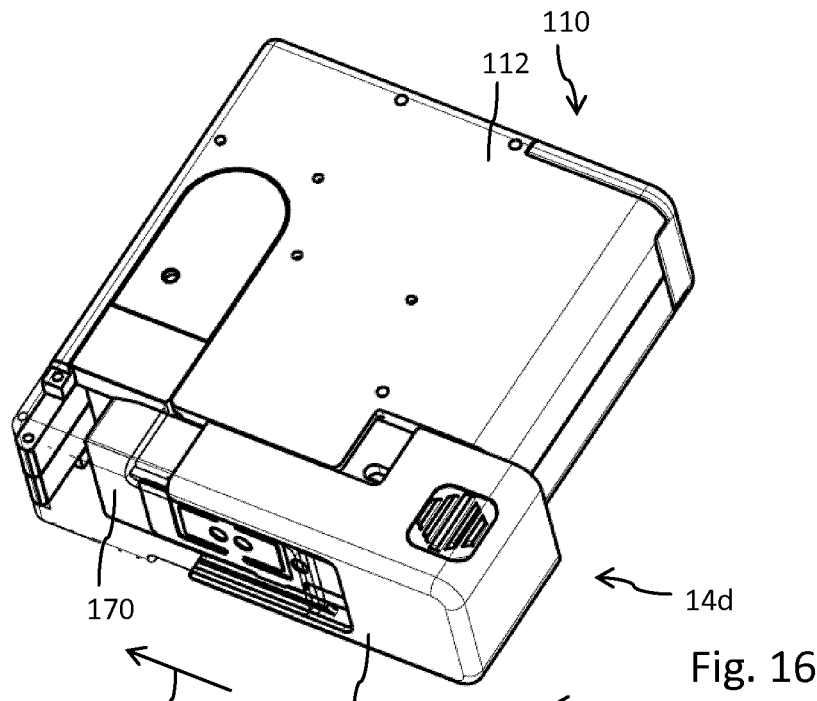
FIG. 16 shows the drug delivery device according to FIGS. 14 and 15 with a closed fastener and FIG. 17 shows the drug delivery device according to FIG. 16 with cartridge and injector in a deployed configuration.

In the undeployed configuration 4 as for instance shown the base 174 of the cartridge 170 at least partially extends beyond the outer circumference of the adjacently-located housing portion of the drug delivery device 110. The fastener 114 is pivotable from the opened configuration 14*c* as shown in FIG. 15 into the closed configuration 14*d* as shown in FIG. 16. The pivotable fastener 114 comprises two portions, namely a base portion 130 by way of which the fastener 114 is pivotably attached to the housing 112 via a hinge 116. Attached to the base portion 130 the fastener 114 comprises a slider 132 forming a free end of the fastener 14 effectively providing a lid 115.

The slider 132 and the base portion 130 are interconnected by means of a planar spring 134 as indicated in FIG. 15 in the same way as with the embodiment according to FIG. 9.

Figure 17:
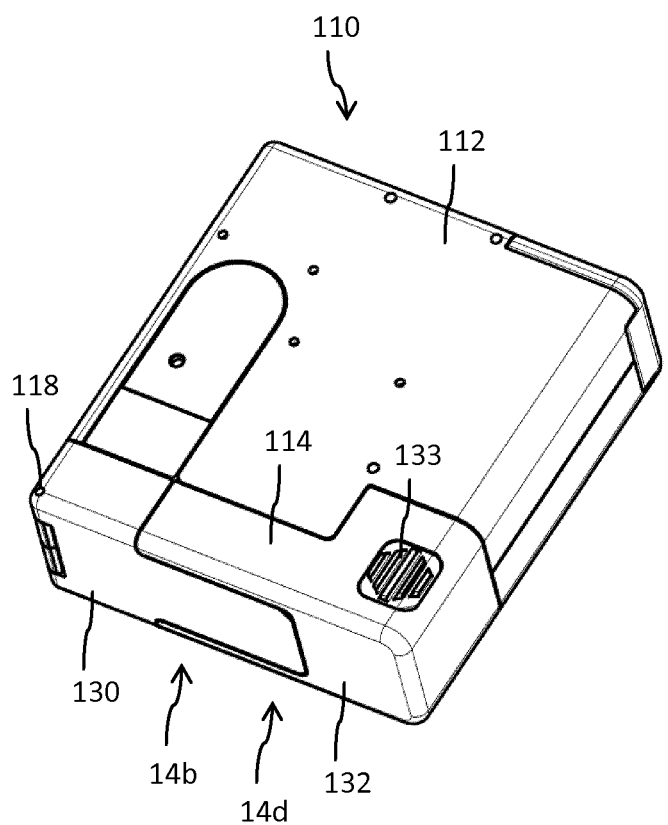

When in closed configuration 14*d*, an inside-facing sidewall portion of the extended slider 132 may directly abut with an outside-facing sidewall portion of the cartridge 170, in particular of its base 174. Now, by displacing the slider 132 into the retracted position 32*b* as shown in FIG. 17 the cartridge 170 is displaced relative to the injector 160 along the deploy direction 1 to establish a fluid communication between the cartridge fluid coupling 190 and the injector fluid coupling 168. Simultaneously and in the same way the slider 132, hence the free end portion of the fastener 114 directly engages with the housing 112 of the drug delivery device 110. As becomes apparent from FIG. 14, inside a sidewall portion of the slider's 132 free end there are located two horizontally extending latch members 126 that are adapted to engage with horizontally and correspondingly-shaped grooves 124 of a latch member 123 extending from the housing 12 of the drug delivery device 110.

The grooves 124 of the latch members 123 are open in a direction opposite the deploy direction 1. They are therefore suitable to receive the corresponding latch members 126 of the slider 132 when the slider 32 is displaced from the extended position 32*a* into the retracted position 32*b* along the deploy direction 1.

Once the medicament contained in the reservoir 180 has been withdrawn thus requiring a replacement of the cartridge 170 the slider 132 is displaceable in a direction opposite to the deploy direction 1, typically by means of the ripples 133 provided at the outer surface of the free end of the slider 132. As soon as the latch members 26, 24 of slider 32 and housing 12 disengage, the fastener 14 will be automatically lifted by a predefined portion due to wings of the spring applying pressure to the upper surface of the cartridge 70.

Then, by pivoting the fastener 114 from the closed configuration 14*d* into the opened configuration 14*c*, a rear panel 131 extending radially from the pivot axis 118 engages with a sidewall portion 171*c* of the housing 71 of the cartridge 70 as becomes apparent from FIG. 14, thereby displacing the cartridge 70 along the linear guiding 72 relative to the injector 60 toward the undeployed configuration 4.

As a consequence, and when reaching e.g. a 90° opening configuration of the fastener 14, the injector 160 and the cartridge 170 are again in their undeployed configuration 4. Hence, the injector fluid coupling 168 is disconnected form the cartridge 170 and its reservoir 180 so that any eventual residual portions of the medicament left in the reservoir 180 are hindered to leave the cartridge 170. Contamination of the environment through and by the medicament can therefore be reduced and prevented.

In addition, the rear panel 131 extending at least partially into the receptacle 120 is of particular benefit to provide an effective safeguard mechanism. When closing the fastener 114, hence when pivoting the fastener 114 from the opened configuration 14c into the closed configuration 14d it is required, that the rear panel 131 may freely enter a recessed portion between the cartridge 170 and the injector 160. In circumstances, wherein the disposable injector 160 and the disposable cartridge 170 should be arranged or inserted into the receptacle 120 already in a deployed configuration 6 closing of the fastener 14 is effectively prevented since the rear panel 131 would evidently collide with the cartridge 170, in particular with its housing 171 that faces away from the base 74.

The invention claimed is:

1. A disposable cartridge for a drug delivery device, the disposable cartridge comprising:
    a flexible bag to accommodate a liquid medicament and having a sidewall and an opening adjacent to the sidewall;
    a socket having a fluid channel in fluid communication with a cartridge fluid coupling, wherein the socket extends into the opening of the flexible bag and comprises an outside facing portion;
    a housing comprising an inside facing sidewall portion complementary shaped to the outside facing portion of the socket, wherein the outside facing portion and the inside facing sidewall portion comprise one of a circular shape, a cylindrical shape, an oval shape, an elliptical shape, a rectangular shape, a flattened round shape, or a flattened oval shape, the inside facing sidewall portion completely covering the flexible bag and having a receptacle to receive the socket with the flexible bag, wherein the sidewall of the flexible bag is fixed between the socket and the receptacle;
    a circumferentially extending groove in the outside facing portion of the socket, wherein the circumferentially extending groove extends all around the outside facing portion of the socket; and
    a sealing ring arranged in the circumferentially extending groove,
    wherein the flexible bag is sealingly press fitted between the sealing ring and the inside facing sidewall portion of the housing, wherein the sealing ring is mechanically squeezed between the outside facing portion of the socket and the inside facing sidewall portion of the housing.

2. The disposable cartridge according to claim 1, wherein the housing is press fitted to the socket.

3. The disposable cartridge according to claim 1, wherein the socket comprises a front face located inside the flexible bag and wherein the fluid channel extends into a central portion of the front face.

4. The disposable cartridge according to claim 3, wherein the socket comprises at least one fluid groove extending from a periphery of the front face into the fluid channel.

5. The disposable cartridge according to claim 1, wherein the housing is substantially opaque.

6. The disposable cartridge according to claim 1, wherein the flexible bag is at least partially transparent and wherein the housing comprises at least one transparent window to allow visual inspection of a content of the flexible bag.

7. The disposable cartridge according to claim 1, wherein the flexible bag comprises a predefined folding structure.

8. The disposable cartridge according to claim 1, wherein the flexible bag comprises a support structure.

9. The disposable cartridge according to claim 1, wherein the flexible bag is attached to the housing at a predefined distance from the socket.

10. The disposable cartridge according to claim 1, wherein at least one of the housing of the disposable cartridge and the socket comprises a linear guiding to engage with at least one of a housing of the drug delivery device and a disposable injector comprising an injection needle, a flexible tube and an injector fluid coupling to engage with the cartridge fluid coupling.

11. The disposable cartridge according to claim 1, wherein the flexible bag contains the liquid medicament, and the liquid medicament comprises one or more pharmaceutically active compounds.

12. The disposable cartridge according to claim 1, wherein the socket and the housing are of a rigid or stiff material.

13. The disposable cartridge according to claim 1, wherein the sealing ring is an O-ring of elastomeric material.

14. A drug delivery device for dispensing of a liquid medicament, comprising:
    a first housing having at least one feeder member;
    a disposable injector comprising an injection needle, a flexible tube and an injector fluid coupling, wherein the injection needle is in fluid communication with the injector fluid coupling via the flexible tube; and
    a disposable cartridge adapted to be attached to the first housing of the drug delivery device, the disposable cartridge comprising
        a flexible bag to accommodate a liquid medicament and having a sidewall and an opening adjacent to the sidewall,
        a socket having a fluid channel in fluid communication with a cartridge fluid coupling, wherein the socket extends into the opening of the flexible bag and comprises an outside facing portion,
        a second housing comprising an inside facing sidewall portion complementary shaped to the outside facing portion of the socket, wherein the outside facing portion and the inside facing sidewall portion comprises one of a circular shape, a cylindrical shape, an oval shape, an elliptical shape, a rectangular shape, a flattened round shape, or a flattened oval shape, the inside sidewall portion completely covering the flexible bag and having a receptacle to receive the socket with the flexible bag, wherein the sidewall of the flexible bag is fixed between the socket and the receptacle;
        a circumferentially extending groove in the outside facing portion of the socket, wherein the circumferentially extending groove extends all around the outside facing portion of the socket; and
        a sealing ring arranged in the circumferentially extending groove,
        wherein the flexible bag is sealingly press fitted between the sealing ring and the inside facing sidewall portion of the second housing, wherein the sealing ring is mechanically squeezed between the outside facing portion of the socket and the inside facing sidewall portion of the second housing.

15. The drug delivery device according to claim 14, wherein the disposable cartridge and the disposable injector are releasably engageable to establish fluid communication via a fastener pivotably attached to the first housing of the drug delivery device.

16. A method of operating a drug delivery device, the method comprising:

mounting a disposable cartridge to the drug delivery device, wherein the disposable cartridge comprises:
- a flexible bag to accommodate a liquid medicament and having a sidewall and an opening adjacent to the sidewall,
- a socket having a fluid channel in fluid communication with a cartridge fluid coupling, wherein the socket extends into the opening of the flexible bag and comprises an outside facing portion,
- a housing comprising an inside facing sidewall portion complementary shaped to the outside facing portion of the socket, wherein the outside facing portion and the inside facing sidewall portion comprises one of a circular shape, a cylindrical shape, an oval shape, an elliptical shape, a rectangular shape, a flattened round shape, or a flattened oval shape, the inside facing sidewall portion completely covering the flexible bag and having a receptacle to receive the socket with the flexible bag, wherein the sidewall of the flexible bag is fixed between the socket and the receptacle,
- a circumferentially extending groove in the outside facing portion of the socket, wherein the circumferentially extending groove extends all around the outside facing portion of the socket, and
- a sealing ring arranged in the circumferentially extending groove,
- wherein the flexible bag is sealingly press fitted between the sealing ring and the inside facing sidewall portion of the housing, wherein the sealing ring is mechanically squeezed between the outside facing portion of the socket and the inside facing sidewall portion of the housing;

establishing fluid communication between the flexible bag within the housing of the disposable cartridge and an injection needle; and activating the drug delivery device to deliver the liquid medicament from the flexible bag.

17. The method of claim 16, further comprising mounting a disposable injector to the drug delivery device, wherein establishing fluid communication between the flexible bag of the disposable cartridge and the injection needle occurs after mounting the disposable cartridge and mounting the disposable cartridge.

18. The method of claim 17, wherein:
- mounting the disposable cartridge to the drug delivery device comprises mounting the disposable cartridge in an undeployed configuration preventing fluid communication between the flexible bag and the injection needle, and
- establishing fluid communication between the flexible bag of the disposable cartridge and the injection needle comprises, after mounting the disposable cartridge and after mounting the disposable injector, deploying the disposable cartridge to a deployed configuration to cause a cannula of the disposable injector to pierce a sealing member of the disposable cartridge to establish fluid communication between the flexible bag of the disposable cartridge and the injection needle.

19. The method of claim 17, wherein mounting the disposable injector to the drug delivery device comprises engaging a feeder member of the drug delivery device to a flexible tube of the disposable injector, and
- activating the drug delivery device comprises causing the feeder member to squeeze the flexible tube to deliver the liquid medicament from the flexible bag.

\* \* \* \* \*